(12) United States Patent
Gordon et al.

(10) Patent No.: US 7,973,189 B2
(45) Date of Patent: Jul. 5, 2011

(54) COBALT NITRIDE LAYERS FOR COPPER INTERCONNECTS AND METHODS FOR FORMING THEM

(75) Inventors: Roy Gerald Gordon, Cambridge, MA (US); Hoon Kim, Cambridge, MA (US); Harish Bhandari, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 394 days.

(21) Appl. No.: 12/100,319

(22) Filed: Apr. 9, 2008

(65) Prior Publication Data

US 2008/0254232 A1    Oct. 16, 2008

Related U.S. Application Data

(60) Provisional application No. 60/922,485, filed on Apr. 9, 2007, provisional application No. 60/998,023, filed on Oct. 5, 2007.

(51) Int. Cl.
*C07F 15/06* (2006.01)
*C23C 16/00* (2006.01)

(52) U.S. Cl. ............. 556/138; 427/248.1; 427/255.394; 106/1.25

(58) Field of Classification Search .................. 556/138; 427/248.1, 255.394
See application file for complete search history.

(56) References Cited

U.S. PATENT DOCUMENTS

| 5,834,058 A | 11/1998 | Wallbridge et al. |
| 6,203,613 B1 | 3/2001 | Gates et al. |
| 7,166,732 B2 | 1/2007 | Xu et al. |
| 2005/0176989 A1 | 8/2005 | Coleman et al. |
| 2006/0141155 A1 | 6/2006 | Gordon et al. |
| 2006/0240187 A1 | 10/2006 | Weidman |

FOREIGN PATENT DOCUMENTS

| WO | WO-2004/007796 | 1/2004 |
| WO | WO-2004/046417 | 6/2004 |
| WO | WO-2009/088522 | 7/2009 |

OTHER PUBLICATIONS

International Search Report issued for PCT/US08/59797, dated on Jun. 11, 2009.

Alavi, "Simulations of the Solid, Liquid, and Melting of 1-*n*-Butyl-4-amino-1,2,4-triazolium Bromide," J. Phys. Chem. B, 2005, 109, pp. 18127-18134.
Bergstrom, et al., "Molecular Descriptors Influencing Melting Point and Their Role in Classification of Solid Drugs," J. Chem. Inf. Comput. Sci., 43, 2003, pp. 1177-1185.
Chae, et al., "The Role of Gas-Phase Reactions During Chemical Vapor Deposition of Copper from (hfac)Cu(tmvs)," J. Electrochem. Soc., vol. 145, No. 12, Dec. 1998, pp. 4226-4233.
de Rouffignac, et al., "Sealing Porous Low-k Dielectrics with Silica," Electromechanical and Solid-State Letters, 7 (12), pp. G306-G308, 2004.
El-Kadri, et al., "Synthesis, Structural Characterization, and Properties of Chromium(III) Complexes Containing Amidinato Ligands and $n^2$-pyrazolato, $n^2$-1,2,4-triazolato, or $n^1$-tetrazolato ligands," Dalton Trans., 2006, pp. 4506-4513.
Hughes, et al., "Why Are Some Properties More Difficult to Predict than Others? A Study of QSPR Models of Solubility, Melting Point, and Log P," J. Chem. Inf. Model, 2008, 48, pp. 220232.
Li et al., "Direct-Liquid-Injection Chemical Vapor Deposition of Nickel Nitride Films and Their Reduction to Nickel Films," Chem. Mater., 2010, 22, pp. 3060-3066.
Li et al., "Formation of Nickel Silicide from Direct-Liquid-Injection Chemical-Vapor-Deposited Nickel Nitride Films," Journal of The Electrochemical Society, 157(6), 2010, pp. H679-H683.
Li, et al., "Synthesis and Characterization of Volatile Liquid Cobalt Amidinates," Dalton Trans., 2008, pp. 2592-2597.
Oussama, et al., "Synthesis, Structural Characterization, and Properties of Chromium(III) Complexes Containing Amidinato Ligands and $n^2$-pyrazolato, $n^2$-1, 2, 4-triazolato, or $n^1$-tetrazolato ligands," Paper, Dalton Transactions, 2006, pp. 4506-4513.
Rao, "Metal Amidinates as Precursors for ALD of Metals and Oxides," presented on Jan. 2007, 32 pages.
Sadique, et al., "Monomeric and Dimeric Amidinate Complexes of Magnesium," Inorg. Chem., 2001, 40, pp. 6349-6355.
Zhefeng Li, "Chapter 7. ALD Fe Synthesis and Characterization of Iron(II) Amidinates as Precursors for ALD Fe: Correlation of Precursors' Properties to their Molecular Structures," Thesis presented on Mar. 19, 2007, 29 pages.

*Primary Examiner* — Porfirio Nazario Gonzalez
(74) *Attorney, Agent, or Firm* — Wilmer Cutler Pickering Hale and Dorr LLP

(57) ABSTRACT

An interconnect structure for integrated circuits incorporates a layer of cobalt nitride that facilitates the nucleation, growth and adhesion of copper wires. The cobalt nitride may deposited on a refractory metal nitride or carbide layer, such as tungsten nitride or tantalum nitride, that serves as a diffusion barrier for copper and also increases the adhesion between the cobalt nitride and the underlying insulator. The cobalt nitride may be formed by chemical vapor deposition from a novel cobalt amidinate precursor. Copper layers deposited on the cobalt nitride show high electrical conductivity and can serve as seed layers for electrochemical deposition of copper conductors for microelectronics.

25 Claims, 3 Drawing Sheets

COBALT NITRIDE LAYERS FOR COPPER INTERCONNECTS AND METHODS FOR FORMING THEM

RELATED INVENTIONS

This application claims the benefit of priority under 35 U.S.C. §119(e) to co-pending U.S. application Ser. No. 60/922,485, filed Apr. 9, 2007, which is hereby incorporated in its entirety by reference.

This application claims the benefit of priority under 35 U.S.C. §119(e) to co-pending U.S. application Ser. No. 60/998,023, filed Oct. 5, 2007, which is hereby incorporated in its entirety by reference.

BACKGROUND

This invention relates to copper interconnections used in microelectronics and methods for depositing metal-containing layers.

Copper is replacing aluminum as the material of choice for wiring of microelectronic devices, such as microprocessors and memories. The copper is normally placed into holes and trenches in an insulator such as silicon dioxide, by an electroplating process. Excess copper is then polished off of the surface of the device. The structure is capped by insulation into which holes and trenches are etched to begin the next level of wiring.

In order for the tiny copper wires to survive the polishing process, the copper must adhere strongly to the insulator. Adhesion must also be maintained through the rest of the production and use of the device. In currently used technology, a bilayer structure of sputtered tantalum nitride (TaN) and tantalum metal (Ta) is used to provide this adhesion. The TaN provides strong adhesion to the insulator, and the Ta adheres strongly to a sputtered seed layer of copper, onto which further copper is electroplated. Ta also prevents oxygen and water from corroding the copper wiring.

The presence of copper in semiconductors such as silicon causes defects that can prevent the proper functioning of transistors formed in the semiconductor. Copper also increases the leakage of current through insulators, such as silicon dioxide, placed between the copper wires. Therefore use of copper wiring demands that efficient diffusion barriers surround the copper wires, to keep the copper confined to its proper locations. The sputtered TaN serves as the diffusion barrier in current technology.

Copper also has a tendency to move in the direction that electrons are flowing in a circuit. This electromigration process can lead to increased electrical resistance or even an open circuit if a sufficiently large void forms within a copper interconnection. Most of this unwanted motion takes place along the surface of the copper. Long lifetimes can be maintained by surrounding the copper interconnections by materials that inhibit electromigration. Tantalum metal (Ta) serves this function on the bottom and sides of currently-used copper interconnections. The tops of copper wiring (those parts that do not connect to an upper level) typically are covered by silicon nitride or silicon carbide, although these materials are not as effective as the Ta in reducing copper electromigration.

In future microelectronic devices, industrial planning, as published yearly in the International Technology Roadmap for Semiconductors (ITRS), calls for narrower wiring based on thinner barrier, adhesion and seed layers. The ITRS projects that currently-used sputtered Cu/TaN/Ta will not be able to meet these projected needs. The poor conformality of sputtered coatings means that thicker than necessary layers are needed near the top of holes and trenches in order to provide sufficient thickness in the lower parts of these structures. The resulting "overhang" near the tops of the features makes it difficult for electroplated copper to fill the holes and trenches without leaving voids, which increases the resistance and exacerbates the electromigration-induced instabilities.

Cobalt (Co) metal has been suggested as a replacement for the Ta adhesion layers in interconnects. Co films can be vapor-deposited (CVD or ALD) with better conformality than sputtered Ta. However when copper is vapor-deposited onto cobalt surfaces, the copper tends to agglomerate into separated nuclei forming relatively rough films with low electrical conductivity.

Ruthenium (Ru) metal has also been suggested as a replacement for the Ta adhesion layers in interconnects. Ru films can be vapor-deposited (CVD or ALD) with better conformality than sputtered Ta. When copper is vapor-deposited onto Ru, the copper layers can be smooth and highly conductive when made under appropriate conditions. However, Ru is an expensive metal, and Ru may not be available in sufficient quantities for large-scale application in interconnects. Also, Ru is not a good diffusion barrier to oxygen.

Thus current interconnect technology lacks a conformal, inexpensive adhesion and oxygen diffusion barrier layer on which smooth and highly conductive layers of copper may be deposited.

SUMMARY

Materials and techniques are disclosed that secure robust adhesion between the copper and the surrounding materials, provide barriers to prevent diffusion of copper out of the wiring and oxygen or water into the wiring, and keep the copper wires from being damaged by the electric current that they carry.

A conformal, inexpensive layer of cobalt nitride ($Co_xN$) is described, onto which smooth and highly conductive layers of copper may be deposited. Compositions of $Co_xN$ typically range from about x=1 to about x=10, and can range, for example, from about 3 to 6. In one embodiment, x is about 4, corresponding to the compound $Co_4N$. x is not required to be an integer.

The $Co_xN$ layers may be deposited by any convenient method, including physical vapor deposition (PVD) and chemical vapor deposition (CVD) methods. CVD can be carried out under deposition conditions that provide conformal coatings.

In one embodiment, a $Co_xN$ layer is deposited by CVD from vapor of a cobalt amidinate, a nitrogen source, e.g., ammonia and a reducing source, e.g., hydrogen gas.

Optionally, a copper diffusion barrier, such as amorphous TaN, TaC, WN, WC or MoN or mixtures thereof may be deposited prior to deposition of the cobalt-containing layer.

A copper layer may be deposited on the $Co_xN$ layer by any convenient method, such as CVD, PVD, chemical reduction or electrochemical-deposition. In one embodiment, a thin copper layer is first deposited by CVD, followed by electrochemical deposition of a thicker layer of copper.

In another embodiment, a copper layers is prepared by first depositing a smooth layer of copper oxynitride layer, followed by reduction of the copper oxynitride to copper metal. The metal layer has low surface roughness and can have RMS roughness of, e.g., less than 5 nm or less than 1 nm.

Use of a $Co_xN$ layer provides a smooth, adherent layer and provides a substrate for formation of highly conductive and strongly adherent copper layers for, e.g., the production of electronic elements, circuits, devices, and systems. Other features and advantages of the invention will be apparent from the following description and accompanying figure, and from the claims.

In another aspect, a metal-comprising layer may be formed by chemical vapor deposition by exposing a substrate to a gaseous mixture comprising vapors of one or more metal amidinate selected from the metals lithium, sodium, potassium, beryllium, calcium, strontium, barium, scandium, yttrium, lanthanum and the other lanthanide metals, titanium, zirconium, hafnium, vanadium, niobium, tantalum, molybdenum, tungsten, manganese, rhenium, iron, ruthenium, cobalt, rhodium, nickel, palladium, silver, zinc, cadmium, tin, lead, antimony and bismuth.

In one or more embodiments, the gaseous mixture comprises an additional reactant, such as a reducing agent, or oxygen- or nitrogen-containing gas.

In one or more embodiments, the gaseous mixture comprises a cobalt amidinate and a vaporous source of nitrogen and hydrogen reducing agent. A cobalt nitride layer can be obtained. Other metal amidinate sources could be used.

In one or more embodiments, the gaseous mixture comprises a copper amidinate. The gaseous mixture may include a vaporous oxygen source and a copper oxide layer can be obtained. Other metal amidinate sources could be used.

In one or more embodiments, the gaseous mixture comprises a copper amidinate and the gaseous mixture may include a vaporous oxygen source and a vaporous nitrogen source. A copper oxynitride layer can be obtained. Other metal amidinate sources could be used.

In still other embodiments, a reducing source such as hydrogen is provided during or after deposition of the copper containing film to form a copper metal layer.

DETAILED DESCRIPTION

Figure 1:
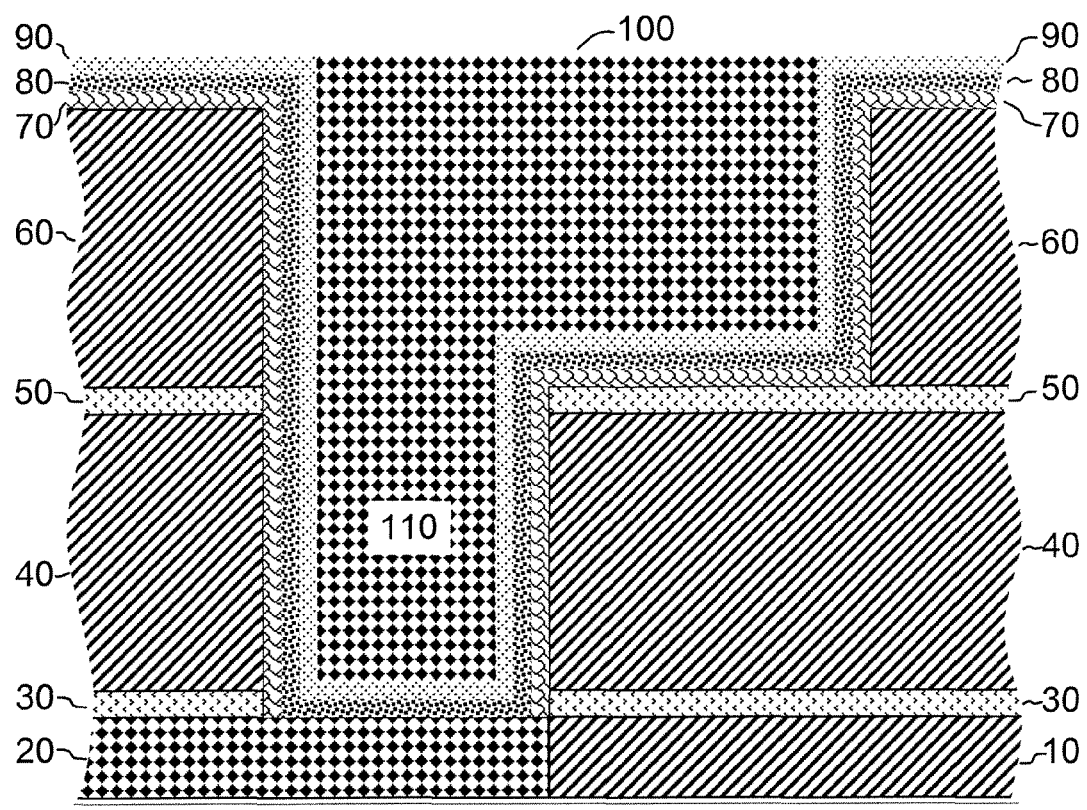
FIG. 1 is a schematic cross section of an interconnect trench and via structured in accordance with the invention.

An electronic device such as an integrated circuit including conductive trenches 100 and vias (holes) 110 is illustrated in schematic cross section in FIG. 1. The structure can be made by conventional photolithography and etching of trenches 100 and vias (holes) 110 in composite insulating layers 30, 40, 50 and 60 according to methods well known in the art.

This structure is constructed on top of a planar surface comprising insulating areas 10 and electrically conducting areas 20 forming the next lower level of wiring. A capping layer 30, typically silicon nitride or silicon carbide, is placed over the surface defined by insulating areas 10 and conducting areas 20, followed by an insulating layer 40, an etch-stop layer 50 and another insulating layer 60. Insulating materials known in the art include silicon dioxide, fluorinated silicon dioxide and silicon oxide carbide, typically made by plasma-enhanced chemical vapor deposition (PECVD). Typical etch-stop materials include PECVD silicon nitride, silicon carbide and silicon carbide-nitride. Trenches 100 and holes (vias) 110 are then etched through the insulating layers by photolithography. Once formed, the trenches and holes are filled with copper to form a next higher level of conductive wiring.

Optionally, the device may be subject to additional processing steps before cobalt nitride or copper deposition. For example, if one or more of the insulating layers 40, 60 contains pores, the openings to these pores can be sealed by the process described in Electrochemical and Solid State Letters, volume 7, pages G306-G-308 (2004), which is incorporated in its entirety by reference. In one embodiment, the layer surfaces are exposed first to a catalytic agent that interacts selectively with the insulating surfaces to form a catalytic surface on at least a portion of the insulating surface. An exemplary catalytic agent is a metal or metalloid compound that includes metal or metalloid amides, amidinates, alkyls, alkoxides and halides. The metal or metalloid can be aluminum, boron, magnesium, scandium, lanthanum, yttrium, titanium, zirconium or hafnium. The exposure time and/or reactivity of the metal or metalloid compound is selected so that the pores deeper inside the dielectric are not exposed to it and/or do not react with it during the time exposed. Next the surface is exposed to one or more silanol compounds, preferably at a temperature above room temperature, to form a silica layer only on the catalytic surface of the substrates. As used herein "silanol" refers to the class of compounds having a silicon atom bonded to one or more hydroxyl (OH) groups; silanols comprise alkoxysilanols, alkoxyalkylsilanols and alkoxysilanediols and their substituted derivatives. The acid sites on the surface catalyze the polymerization of the silanol into a layer of silica, which is deposited onto the exposed surfaces of the insulating material. When the exposed insulating material includes surfaces within and surrounding pores, the silica bridges over and seals the outer pores. The result of this pore-sealing process is a smooth and clean silica layer onto which may be deposited a barrier against the diffusion of copper.

The diffusion barrier 70 may include a thin layer of amorphous material such as tantalum nitride ($TaN_y$), tungsten nitride ($WN_y$), tantalum carbide, tungsten carbide ($WC_y$) or molybdenum nitride (MoN). Typically, y is approximately 1. One non-limiting purpose of the diffusion barrier is to prevent the escape of copper from the structure during use. Another non-limiting purpose of the diffusion barrier is to promote adhesion between the subsequently deposited $Co_xN$ layer and the underlying insulator. The diffusion barrier may be deposited by any effective method, such as sputtering or CVD.

CVD may be a preferred method because of the better conformality of CVD diffusion barriers. By way of example, vapors of bis(alkyl-imido)bis(dialkylamido) tungsten(VI) are reacted with ammonia gas, $NH_3$, on the heated surface of a substrate, to form coatings of tungsten nitride. In some embodiments, the reaction may be carried out in a manner to form films on substrates that may include holes or trenches.

Tungsten compounds may have the general formula 1, in which R″ represents alkyl groups, fluoroalkyl groups or alkyl groups substituted with other atoms or groups, preferably selected to enhance the volatility of the compound, where R″ is any one of $R^1$ through $R^6$. The R″ may be the same or different from each other.

1

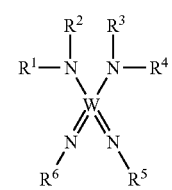

In certain embodiments, R″ represents alkyl groups, arylalkyl groups, alkenylalkyl groups, alkynylalkyl groups, fluoroalkyl groups or alkyl groups substituted with other atoms or groups selected to enhance the volatility of the compound, where R" is any one of $R^1$ through $R^6$ and where the R" may be the same or different from each other.

Suitable bis(alkyl-imido)bis(dialkylamido) tungsten(VI) compounds include those in which the alkyl groups $R^5$ and $R^6$ in structure 1 have a tertiary carbon attached to the imido nitrogen, as is shown by the compounds of the general structure 2:

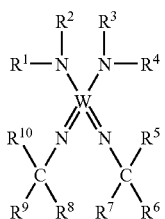

Methyl groups can be selected for all the R" in the general formula 2 given above. In one or more embodiments, the tungsten compound is bis(tert-butylimido)bis(dimethylamido) tungsten(VI); $(^tBuN)_2(Me_2N)_2W$.

Other suitable compounds include the compound obtained by selecting in formula 2 $R^1$, $R^4$, $R^5$, $R^6$, $R^7$, $R^8$, $R^9$ and $R^{10}$ to be methyl groups, and $R^2$ and $R^3$ to be ethyl groups, i.e., bis(ethylmethylamido)bis(tert-butylimido)tungsten(VI), and the compound obtained by selecting in formula 1 the groups $R^1$, $R^2$, $R^3$ and $R^4$ to be methyl groups, and $R^5$ and $R^6$ to be isopropyl groups, e.g., bis(dimethylamido)bis(isopropylimido)tungsten(VI). Two or more alkyl groups may be linked to form cyclic compounds, and the groups may contain some degree of unsaturation, e.g., aryl, alkenyl or alkynyl groups. In addition, the compound can contain neutral or anionic ligands. Many neutral ligands are known. Exemplary neutral ligands include, e.g., alkenes, alkynes, phosphines and CO. Many anionic ligands are known. Exemplary anionic ligands include methyl, methoxy and dimethylamido groups. These structures are believed to facilitate deposition of films with low carbon content because of the facile beta-hydrogen elimination reactions for alkyl groups with tertiary carbon. In other embodiments, the tungsten metal may be substituted by molybdenum. Bis(alkyl-imido)bis(dialkylamido) tungsten (VI) and molybdenum (IV) compounds are commercially available or may be made by any conventional method. See, e.g., International Application WO 2004/007796, which is incorporated by reference.

Tungsten nitride films are deposited under conditions that produce good adhesion between the deposited tungsten nitride film and a substrate onto which it is deposited. In one or more embodiments, vapor deposition of highly uniform tungsten nitride films is accomplished over a range of conditions such as concentrations of reactants and position of the substrate inside the reactor. In one or more embodiments, substrates are coated at relatively low temperatures from about 200° C. to 500° C. In some embodiments, the WN film is prepared on a substrate maintained at a temperature between about 300° C. and about 500° C.

In other embodiments, the tungsten nitride layer is formed using atomic layer deposition (ALD). The ALD process includes one or more cycles of exposing the substrate to a vapor of a of bis(alkyl-imido)bis(dialkylamido) tungsten(VI) compound, wherein at least a portion of the vapor adsorbs on the surface of the substrate by a self-limiting process; and then exposing the substrate to ammonia vapor that activates the surface so that the surface is prepared to react with additional quantities of bis(alkyl-imido)bis(dialkylamido) tungsten(VI) compound. Additional details of an exemplary ALD process are found in International Application WO 2004/007796, which is incorporated in its entirety by reference.

Optionally, directional ion etching may be used to remove some or all of the barrier material that overlies conductive material 20, such as copper, at the bottom of via holes. This step allows connections with lower resistance between the via and the underlying copper layers 20. FIG. 1 illustrates the device in which the diffusion barrier layer is removed above copper layer 20.

Next, a layer of cobalt nitride ($Co_xN$) 80 is deposited onto the barrier layer. The cobalt nitride layer 80 may be applied using any convenient method. The $Co_xN$ layers generally have values of x between about 1 and 10, for example, between about 2 and 6, or between about 3 and 5. In one or more embodiments, a compound in the cobalt nitride layer is $Co_4N$. x need not be an integer.

In some embodiments, the $Cu_4N$ layer is polycrystalline. This structure promotes epitaxial growth of copper grains with the same orientation. The strong adhesion between these epitaxially oriented copper grains and the cobalt nitride is believed to enhance the stability and lifetime of the interconnect structures.

In one or more embodiments, CVD is used for depositing the $Co_xN$ layer, but other methods, such as sputtering are also contemplated. The layer 90 is a copper seed layer, which may be deposited by any convenient method known in the art, including a chemical method such as CVD or physical methods such as sputtering or PVD. The trenches 100 and vias 110 are then filled with copper using conventional methods, such as electroplating or electroless deposition, which are well-known in the art.

In certain embodiments, the $Co_xN$ diffusion barrier layer is deposited by CVD. In one CVD method, a cobalt amidinate is mixed with a vaporous source of nitrogen and hydrogen and exposed to a heated substrate to deposit a conformal cobalt nitride layer. The composition x of the $Co_xN$ layer can be adjusted by changing the composition of the CVD gas mixture. Increasing the ratio of $H_2$ to $NH_3$ in the CVD gas mixture increases the value of x. The composition can also be adjusted by annealing the layer after deposition at a temperature of 180 to 400° C. Increasing the ratio of $H_2$ to $NH_3$ in the anneal atmosphere also increases the value of x.

In one or more embodiments, cobalt amidinates have the structure, $[M(AMD)_x]$, where M is Co, AMD is an amidinate and x=2 or 3. Some of these compounds have a structure 3,

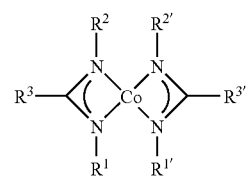

in which $R^1$, $R^2$, $R^3$, $R^{1'}$, $R^{2'}$ and $R^{3'}$ are groups made from one or more non-metal atoms. In some embodiments, $R^1$, $R^2$, $R^3$, $R^{1'}$, $R^{2'}$ and $R^{3'}$ may be the same or different and may be chosen independently from hydrogen, alkyl, aryl, alkenyl, alkynyl, trialkylsilyl or fluoroalkyl groups. In some embodiments, $R^1$, $R^2$, $R^3$, $R^{1'}$, $R^{2'}$ and $R^{3'}$ may be the same or different and are each independently alkyl or haloalkyl, e.g., fluoroalkyl, or silylalkyl groups containing 1 to 4 carbon atoms. In one or more embodiments, the cobalt amidinate comprises cobalt(II) bis(N,N'-diisopropylacetamidinate), corresponding to taking $R^1$, $R^2$, $R^{1'}$ and $R^{2'}$ as isopropyl groups, and $R^3$ and $R^{3'}$ as methyl groups in the general formula 3. In addition, the compound can contain neutral or anionic ligands. Many neutral ligands are known. Exemplary neutral ligands include, e.g., alkenes, alkynes, phosphines and CO. Many anionic ligands are known. Exemplary anionic ligands include methyl, methoxy and dimethylamido groups.

In an exemplary CVD method, bis(N,N'-diisopropylacetamidinato)cobalt(II) vapor is mixed with ammonia ($NH_3$) gas and dihydrogen gas ($H_2$) at a temperature of about 80° C., and this vapor mixture is flowed over the partially completed interconnect structure which has been heated to a temperature between 100 and 300° C., preferably between 150 and 250° C. and most preferably between 170 and 200° C. A $Co_xN$ layer is formed on the diffusion barrier. In some embodiments, the $Co_xN$ layer has a thickness of about 1 to 4 nm, or a thickness of about 2 to 3 nm.

An alternative CVD precursor for making cobalt nitride is bis(N-tert-butyl-N'-ethyl-propionamidinato)cobalt(II), corresponding to $R^1$ and $R^{1'}$ being tert-butyl and $R^2$, $R^{2'}$, $R^3$ and $R^{3'}$ being ethyl, which is a liquid at room temperature. Liquid precursors are easier to purify, handle and vaporize than solid precursors. Copper amidinates are commercially available or may be made by any conventional method. See, e.g., International Application WO 2004/046417, which is incorporated by reference.

Other methods of depositing the $Co_xN$ layer can be used. For example, an ALD process in which the heated substrate is exposed to alternating vapors of a metal amidinate and reducing gas/nitrogen containing compound can be used to prepare the $Co_xN$ compound. See, e.g., International Application WO 2004/046417 for further information, which is incorporated in its entirety by reference.

A copper conductor can be placed on the cobalt nitride layer by any convenient method, including physical methods, such as sputtering, and chemical methods, such as CVD or electroless deposition. The chemical methods typically provide better conformality.

CVD of copper can be carried out by established methods known in the art. For example, copper(I) 1,1,1,5,5,5-hexafluoroacetylacetonate trimethylvinylsilane (Cuprasélect™) is a source for CVD of copper, whose use is described, for example, in the Journal of the Electrochemical Society, volume 145, pages 4226-4233 (1998), which is hereby incorporated by reference. CVD of copper using copper(I) N,N'-di-sec-butylacetamidinate is described in WO 2004/046417, and is hereby incorporated by reference in its entirety. A short reaction time (less than a few minutes) at low temperatures (less than 200° C.) in the presence of a reducing gas, e.g., hydrogen, produces relatively smooth copper metal films (root mean square roughness less than a few nanometers).

In yet another embodiment, the copper layer may be formed by depositing a copper oxynitride layer and reducing the resultant layer to a copper metal. Copper oxide or nitride has better wettability than metallic copper, which results in higher nucleation density, and continuous thin layers with smoother and more continuous morphology than metallic copper. When the copper oxynitride is converted to metallic copper under conditions that do not increase agglomeration of copper, the smooth morphology of the precursor layer can be transferred to the copper metal layer. Reduction of the deposited thin film is conducted at a low temperature to avoid or reduce agglomeration of the copper that can result in a rough or discontinuous film.

For example, (N,N'-di-sec-butyl-acetamidinato)copper(I) dimer can be used as a source for CVD of copper as described above in combination with an nitrogen source such as ammonia or hydrazine and an oxygen source such as $O_2$, water vapor, ozone or a peroxycompound such as hydrogen peroxide. Both oxygen and nitrogen are incorporated into the film when a mixture of ammonia and water vapor are used as reactant gases during deposition. A short reaction time (less than a few minutes) at low temperatures (less than 200° C.) produces a very smooth copper oxynitride film (root mean square roughness 0.4 to 0.6 nanometer). Reduction, for example, by exposure to hydrogen plasma at a temperature <50° C., reduces the film to copper metal and results in a film of exceptional smoothness. The use of a strong reducing agent lowers the temperature of reaction and facilitates the formation of a smooth metal layer. Root mean square roughness of less than about 1 nm, and even 0.5 nm to 0.8 are possible. Reduction may also be carried out by chemical reduction in solution or by electrochemical reduction. For example, copper oxynitride may be reduced by electrolysis in a neutral or basic electrolyte solution.

Once a thin, conformal seed layer of copper has been formed on the cobalt nitride by one of these methods, electrochemical deposition can be used to fill the trenches and vias with copper. Electrochemical deposition has the advantages that it can provide pure copper without voids or seams in a cost-effective process. Conventional methods for depositing copper are used.

In another aspect, metal-containing films can be prepared by CVD of a metal amidinate vapor mixed with an appropriate reactive gas. A metal-comprising layer may be formed by chemical vapor deposition by exposing a substrate to a gaseous mixture comprising vapors of one or more metal amidinate selected from the metals lithium, sodium, potassium, beryllium, calcium, strontium, barium, scandium, yttrium, lanthanum and the other lanthanide metals, titanium, zirconium, hafnium, vanadium, niobium, tantalum, molybdenum, tungsten, manganese, rhenium, iron, ruthenium, cobalt, rhodium, nickel, palladium, silver, zinc, cadmium, tin, lead, antimony and bismuth.

In one aspect, a thin film comprising a metal is prepared by exposing a heated substrate to a gaseous mixture comprising vapors of one or more volatile metal amidinate compounds and a reducing gas or vapor, to form a metal coating on the surface of the substrate. In one or more embodiments, the reducing gas includes hydrogen or formic acid.

In one aspect, a thin film comprising a metal nitride is prepared by exposing a heated substrate to a gaseous mixture comprising vapors of one or more volatile metal amidinate compounds and a nitrogen-containing gas or vapor, to form a metal nitride coating on the surface of the substrate. In one or more embodiments, the nitrogen-containing gas includes ammonia or hydrazine.

In another aspect, a thin film comprising a metal oxide is prepared by exposing a heated substrate to a gaseous mixture comprising vapors one or more volatile metal amidinate compounds and an oxygen-containing gas or vapor, to form a metal oxide coating on the surface of the substrate. In one or more embodiments, the oxygen-containing gas includes water, oxygen, ozone or hydrogen peroxide.

In some embodiments, the metal oxide is copper oxide and a thin copper oxide film is prepared by exposing a heated substrate to a gaseous mixture comprising vapors one or more volatile copper amidinate compounds and an oxygen-containing gas or vapor. For example, the metal amidinate precursor is (N,N'-di-sec-butyl-acetamidinato)copper(I) dimer.

In some embodiments, the metal oxide is copper oxynitride and a thin copper oxynitride film is prepared by exposing a heated substrate to a gaseous mixture comprising vapors one or more volatile copper amidinate compounds and an oxygen-containing gas or vapor and a nitrogen containing vapor such as ammonia or hydrazine. For example, the metal amidinate precursor is (N,N'-di-sec-butyl-acetamidinato)copper(I) dimer.

In one or more embodiments, a metal thin film is prepared by reducing the as-formed metal oxide or oxynitride thin film. For example, copper oxide and copper oxynitride thin films may be reduced by a reducing agent such as hydrogen plasma, dihydrogen gas or formic acid vapor to obtain a copper metal thin film.

In one or more embodiments, volatile metal(I) amidinates, $[M(I)(AMD)]_x$, where x=2, 3 are precursors for vapor deposition. Some of these compounds have a dimeric structure 4,

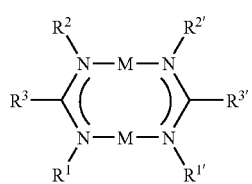

in which $R^1$, $R^2$, $R^3$, $R^{1'}$, $R^{2'}$ and $R^{3'}$ are groups made from one or more non-metal atoms. In some embodiments, $R^1$, $R^2$, $R^3$, $R^{1'}$, $R^{2'}$ and $R^{3'}$ may be different and may be chosen independently from hydrogen, alkyl, aryl, alkenyl, alkynyl, trialkylsilyl or fluoroalkyl groups. In some embodiments, $R^1$, $R^2$, $R^3$, $R^{1'}$, $R^{2'}$ and $R^{3'}$ are each independently alkyl or fluoroalkyl or silylalkyl groups containing 1 to 4 carbon atoms. Non-limiting examples of monovalent metals include copper(I), silver(I), gold(I), and iridium(I). In one or more embodiments, the metal amidinate is a copper amidinate, and the copper amidinate comprises copper(I) N,N'-diisopropylacetamidinate, corresponding to taking $R^1$, $R^2$, $R^{1'}$ and $R^{2'}$ as isopropyl groups, and $R^3$ and $R^{3'}$ as methyl groups in the general formula 1. In one or more embodiments, the metal(I) amidinate is a trimer having the general formula $[M(I)(AMD)]_3$. In addition, the compound can contain neutral ligands. Many neutral ligands are known. Exemplary neutral ligands include, e.g., alkenes, alkynes, phosphines and CO.

In one or more embodiments, divalent metal precursors for vapor deposition include volatile metal(II) bis-amidinates, $[M(II)(AMD)_2]_x$, where x=1, 2. These compounds may have a monomeric structure 5,

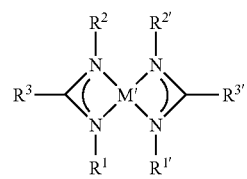

in which $R^1$, $R^2$, $R^3$, $R^{1'}$, $R^{2'}$ and $R^{3'}$ are groups made from one or more non-metal atoms. In one or more embodiments, dimers of this structure, e.g., $[M(II)(AMD)_2]_2$, may also be used. In some embodiments, $R^1$, $R^2$, $R^3$, $R^{1'}$, $R^{2'}$ and $R^{3'}$ may be chosen independently from hydrogen, alkyl, aryl, alkenyl, alkynyl, trialkylsilyl, or fluoroalkyl groups. In some embodiments, $R^1$, $R^2$, $R^3$, $R^{1'}$, $R^{2'}$ and $R^{3'}$ are each independently alkyl or fluoroalkyl or silylalkyl groups containing 1 to 4 carbon atoms. Non-limiting examples of divalent metals include cobalt, iron, nickel, manganese, ruthenium, zinc, titanium, vanadium, europium, calcium, strontium, barium, tin and lead. In one or more embodiments, the metal(II) amidinate is a cobalt amidinate, and the cobalt amidinate comprises cobalt(II) bis(N,N'-diisopropylacetamidinate), corresponding to taking $R^1$, $R^2$, $R^{1'}$ and $R^{2'}$ as isopropyl groups, and $R^3$ and $R^{3'}$ as methyl groups in the general formula 2. In addition, the precursor can contain neutral ligands. Many neutral ligands are known. Exemplary neutral ligands include, e.g., alkenes, alkynes, phosphines and CO.

In one or more embodiments, precursors for vapor deposition of trivalent metals include volatile metal(III) tris-amidinates, $M(III)(AMD)_3$. Typically, these compounds have a monomeric structure 6,

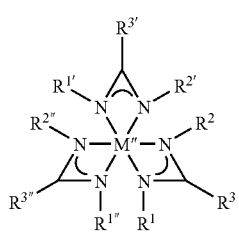

in which $R^1$, $R^2$, $R^3$, $R^{1'}$, $R^{2'}$, $R^{3'}$, $R^{1''}$, $R^{2''}$ and $R^{3''}$ are groups made from one or more non-metal atoms. In some embodiments, $R^1$, $R^2$, $R^3$, $R^{1'}$, $R^{2'}$, $R^{3'}$, $R^{1''}$, $R^{2''}$ and $R^{3''}$ may be chosen independently from hydrogen, alkyl, aryl, alkenyl, alkynyl, trialkylsilyl, halogen or partly fluorinated alkyl groups. In some embodiments, $R^1$, $R^2$, $R^3$, $R^{1'}$, $R^{2'}$, $R^{3'}$, $R^{1''}$, $R^{2''}$ and $R^{3''}$ are each independently alkyl groups containing 1 to 4 carbon atoms. Non-limiting examples of trivalent metals include lanthanum, praseodymium and the other lanthanide metals, yttrium, scandium, titanium, vanadium, niobium, tantalum, iron, ruthenium, cobalt, rhodium, iridium, antimony and bismuth. In one or more embodiments, the metal(III) amidinate is a lanthanum amidinate, and the lanthanum amidinate comprises lanthanum(III) tris(N,N'-di-tert-butylacetamidinate), corresponding to taking $R^1$, $R^2$, $R^{1'}$, $R^{2'}$, $R^{1''}$ and $R^{2''}$ as tert-butyl groups and $R^3$, $R^{3'}$ and $R^{3''}$ as methyl groups in the general formula 6. In addition, the precursor can contain neutral ligands. Many neutral ligands are known. Exemplary neutral ligands include, e.g., alkenes, alkynes, phosphines and CO.

As used herein, metal amidinates having the same ratio of metal to amidinate as the monomer, but varying in the total number of metal/amidinate units in the compound are referred to as "oligomers" of the monomer compound. Thus, oligomers of the monomer compound $M(II)AMD_2$ include $[M(II)(AMD)_2]_x$, where x is 2, 3, etc. Similarly, oligomers of the monomer compound $M(I)AMD$ include $[M(I)AMD]_x$, where x is 2, 3, etc.

Example 1

CVD of WN, Co$_4$N and Cu

A silicon wafer with a SiO$_2$ insulating layer on top was used as the substrate. Trenches and holes were etched in some areas of the SiO$_2$ layer.

Tungsten nitride was deposited by CVD by exposing a vapor mixture of about 0.05 Torr bis(tert-butylimido)bis(dimethylamido)tungsten(VI), 0.5 Torr ammonia and 0.5 Torr nitrogen to a substrate temperature of 390° C. for 1 minute. A diffusion barrier of WN about 2 nm thick was deposited.

Figure 2:
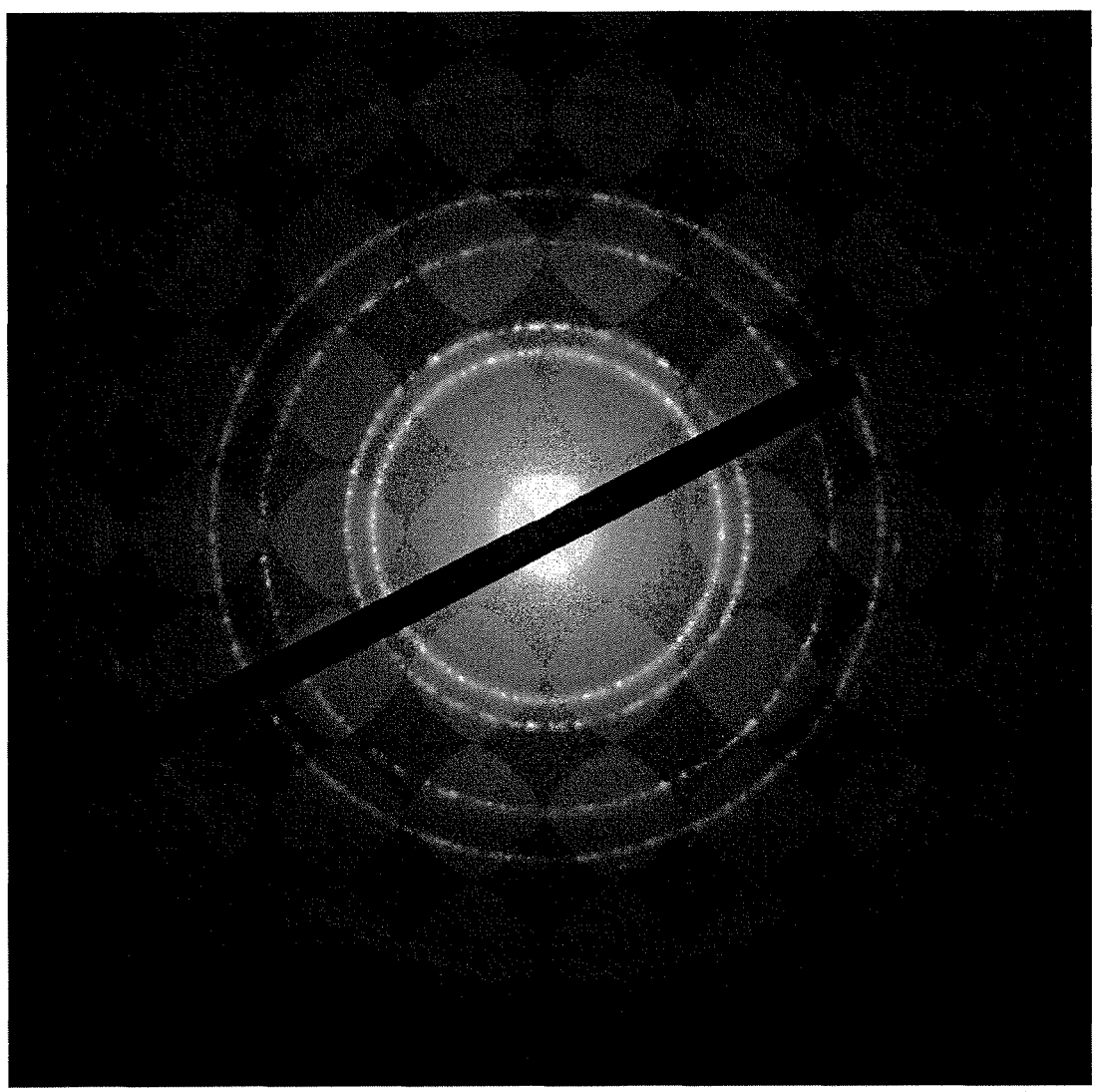
FIG. 2 is an electron diffraction pattern of a $Co_4N$ film.
Figure 3:
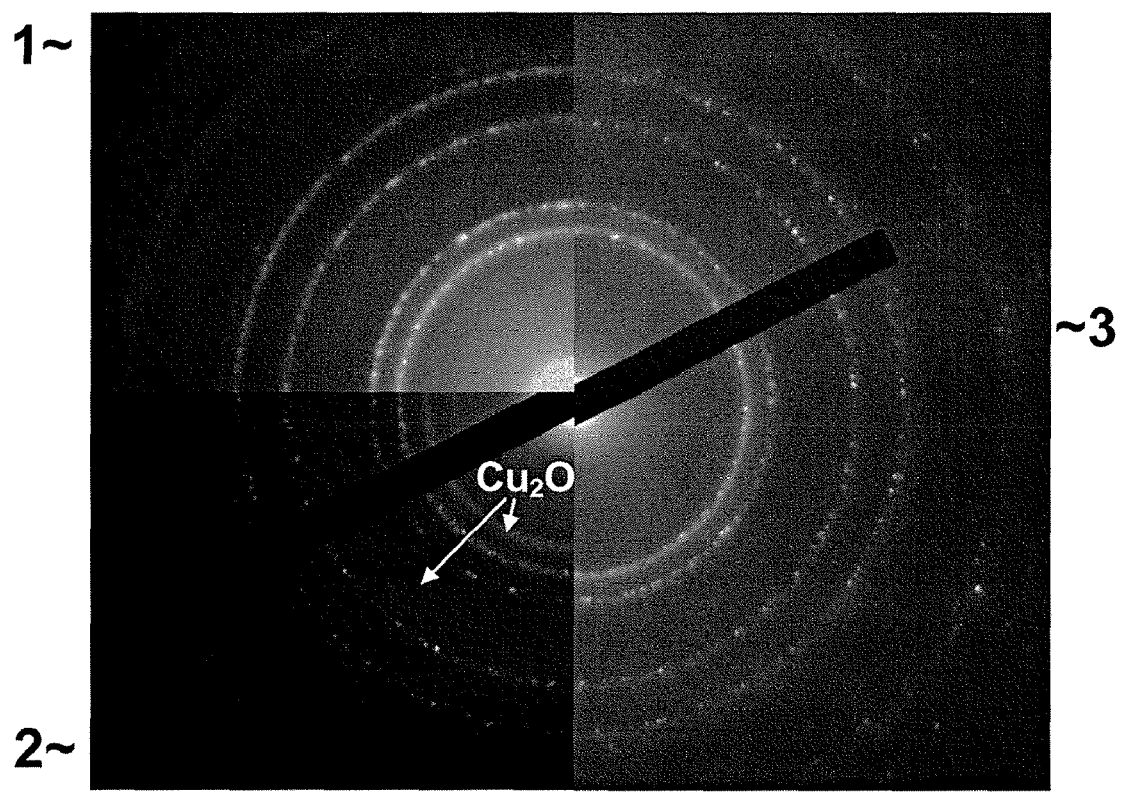
FIG. 3 is an electron diffraction pattern of a bilayer film containing layers of $Co_xN$ and Cu depicted on the right half of FIG. 3 (panel 3), along with comparison electron diffraction patterns of a $Co_4N$ film alone (1, upper left quadrant of FIG. 3) and a copper metal film (2, lower left quadrant in FIG. 3) that also contained a $Cu_2O$ layer.

Cobalt nitride was deposited by CVD a vapor mixture of about 0.03 Torr bis(N-tert-butyl-N'-ethyl-propionamidinato)cobalt(II), 0.2 Torr ammonia, 0.3 Torr hydrogen and 0.5 torr nitrogen to a substrate temperature of 186° C. for 4 minutes. A layer comprising $Co_xN$ about 2 nm thick was deposited. For analysis of this $Co_xN$ material, thicker layers were deposited onto glassy carbon substrates and then subjected to Rutherford Backscattering Analysis (RBS). Cobalt and nitrogen were detected in the film with an atomic ratio x~4, along with a small amount of oxygen coming from exposure to the atmosphere after deposition. A similarly deposited $Co_4N$ film about 20 nm thick was placed in a transmission electron microscope, which was used to obtain the electron diffraction pattern shown in FIG. 2. The observed diffraction rings can all be indexed by a close-packed face-centered cubic structure in which the cobalt atoms have the same positions as the copper atoms in copper metal, and nitrogen atoms are placed at the body centers. To confirm the coincidence of the $Co_4N$ and Cu structures, a bilayer film of 20 nm $Co_4N$ and 20 nm Cu was also subject to electron diffraction. The resulting electron diffraction pattern is shown on the right half of FIG. 3 (panel 3), along with comparison electron diffraction patterns of a the $Co_4N$ film alone (1, upper left quadrant of FIG. 3) and a copper metal film (2, lower left quadrant in FIG. 3) that also contained a $Cu_2O$ layer. The good agreement between all three of these electron diffraction patterns confirms that there is a good coincidence between the structures of $Cu_4N$ and Cu.

A copper seed layer was made by exposing a vapor mixture of about 0.4 Torr (N,N'-di-sec-butyl-acetamidinato)copper(I) dimer, 0.8 Torr hydrogen and 0.8 Torr nitrogen at a substrate temperature of 186° C. for 2 minutes. A layer of copper about 7 nm thick was deposited.

The sheet resistance of these layers is 30 ohms per square, measured on planar areas of the substrates. On these seed layers, electrochemical deposition of additional copper on the surface and within trenches and holes can be carried out using known techniques. The $Co_4N$ layer was found to be a good barrier against diffusion of oxygen and water.

Comparative Example

CVD of WN, Co and Cu

Example 1 is repeated except that cobalt metal is deposited instead of cobalt nitride. The cobalt metal was deposited on WN previously formed as in Example 1. The Co was made by CVD for 20 minutes from a vapor mixture of about 0.03 Torr bis(N-tert-butyl-N'-ethyl-propionamidinato)cobalt(II), 0.5 Torr hydrogen and 0.5 torr nitrogen at a substrate temperature of 240° C. A layer of Co about 2 nm thick was deposited on the WN. After the Co was deposited, copper was deposited as in Example 1.

The sheet resistance of these layers is about 10 times higher than the layers obtained in Example 1. This comparison shows the unexpected advantage of $Co_xN$ over cobalt metal in nucleating a more conductive copper seed layer.

Example 2

CVD of WN, $Co_4N$+$Co_3N$ and Cu

Example 1 is repeated except that during the $Co_xN$ deposition, 0.3 Torr ammonia, 0.2 Torr hydrogen was used. The deposition was carried out for 4 minutes, which was long enough to produce a $Co_xN$ layer about 2 nm thick. RBS analysis on a thicker film produced under the same conditions determined that the cobalt to nitrogen ratio x was between 3 and 4. Electron diffraction confirmed that the major phase of this film is $Co_4N$, along with some hexagonal $Co_3N$.

After deposition of the copper seed layer, the sheet resistance was about 2.4 times higher than the layers produced in Example 1. This example shows that a $Co_3N$+$Co_4N$ mixture produces a more conductive copper film than pure Co, but not as pure conductive as $Co_4N$ does.

Example 3

CVD of WN, $Co_3N$ and Cu

Example 1 is repeated except that during the $Co_xN$ deposition, 0.5 Torr of ammonia was used and no hydrogen was used. The deposition was carried out for 4 minutes, which was long enough to produce a $Co_xN$ layer about 2 nm thick. RBS analysis on a thicker film produced under the same conditions determined that the cobalt to nitrogen ratio x was approximately 3. Electron diffraction confirmed that the structure of the film was hexagonal $Co_3N$.

After deposition of the copper seed layer, the sheet resistance was about 4 times higher than the layers produced in Example 1. This example shows that $Co_3N$ produces a more conductive film than pure Co, but not as conductive as $Co_4N$ does.

Example 4

CVD of WN, $Co_4N$ and Cu

Example 1 is repeated except that the copper layer is deposited from (1,1,1,5,5,5-hexafluoroacetoacetonato)copper(I) trimethylvinylsilane. The copper seed layer is made by CVD for 30 seconds from a vapor mixture of about 0.4 Torr (1,1,1,5,5,5-hexafluoroacetoacetonato)copper(I) trimethylvinylsilane, 1 Torr hydrogen and 2 Torr nitrogen at a substrate temperature of 100° C. A layer of copper layer about 7 nm thick is deposited.

The copper layers deposited in these examples show strong adhesion to the cobalt nitride. Additional copper can be electroplated onto these thin copper layers by procedures known in the art. The electroplated structures can be polished to provide interconnections for microelectronic devices.

Example 5

Synthesis of bis(N-tert-butyl-N'-ethyl-propionamidinato)cobalt(II) was carried out by the following four reactions. All reactions and manipulations were conducted under a pure nitrogen atmosphere using either an inert atmosphere box or standard Schlenk techniques. Tetrahydrofuran (THF), methylene chloride ($CH_2Cl_2$) and pentane were dried using an Innovative Technology solvent purification system and stored over 4 Å molecular sieves. Butyllithium, tert-butyl chloride, ethylamine, propionitrile, $CoCl_2$ and $FeCl_3$ were used as received.

(a) Synthesis of N-tert-butyl-N'-ethyl-propionamidine by coupling tert-butyl chloride, ethylamine and propionitrile with ferric chloride

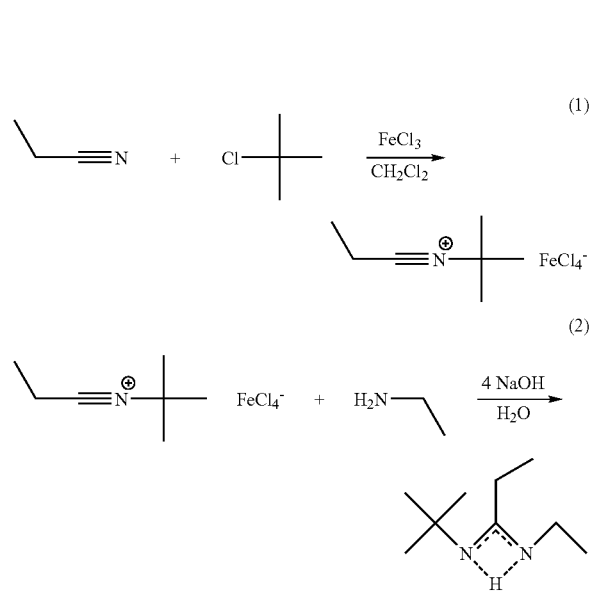

0.30 mol (50 g) anhydrous FeCl$_3$ was suspended in 250 mL dry CH$_2$Cl$_2$. After 2 minutes, the solution was cooled to –40° C. and 21.4 mL (0.30 mol) of anhydrous propionitrile was added at once with magnetic stirring. The ferric chloride went into solution and the color of the medium turned dark red. The solution was cooled to –78° C.; then anhydrous tert-butyl chloride (33 ml, 0.30 mol) was added at once. A brown ocher precipitate formed within a few minutes; presumably it was N-tert-butylacetonitrilium tetrachloroferrate. The reaction medium was then maintained at –78° C. Ethylamine was condensed (13.5 g, 0.30 mol) into the stirred reaction mixture; an exothermic reaction ensued. It remained stirring while it warmed to ambient temperature. It was then cooled to –10° C. and poured into 0.25 L of 5 M NaOH stirred in an ice bath. The resulting mixture was extracted twice with CHCl$_3$. The organic phase was washed twice with 100 ml of water. The organic solution was dried over MgSO$_4$, and then evaporated to yield a light yellow liquid. The crude amidine thus obtained was then purified by distillation (40° C./0.06 Torr) to give a colorless liquid. Yield 38 g, 81%. $^1$H NMR (CDCl$_3$, 25° C., ppm): 1.0-1.1 (2t, 6H, CH$_2$CH$_3$), 1.30 (s, 9H, C(CH$_3$)$_3$), 2.03 (q, 2H, CCH$_2$CH$_3$), 3.16 (q, 4H, NCH$_2$CH$_3$).

(b) Synthesis of bis(N-tert-butyl-N'-ethyl-propionamidinato)cobalt(II) by reaction of N-tert-butyl-N'-ethyl-propionamidine with butyllithium and cobalt (II) chloride

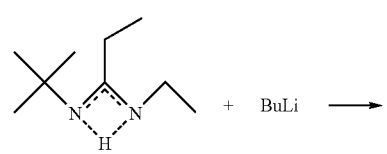

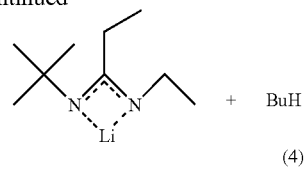

A solution of butyllithium (1.6 M in hexanes, 81 mL, 0.13 mol) was added dropwise to a solution of N-tert-butyl-N'-ethyl-propionamidine (20.3 g, 0.13 mol) in 0.2 L of THF at –78° C. The mixture was warmed to room temperature and stirred for 4 hrs. This resultant solution was then added to a solution of cobalt(II) chloride, CoCl$_2$, (8.44 g, 0.065 mol) in 0.1 L of THF at room temperature. The reaction mixture was stirred for 12 hrs under nitrogen atmosphere. All volatiles were then removed under reduced pressure, and the resulting solid was extracted with pentane. The pentane extract was filtered through a pad of Celite on a glass frit. The pentane was removed under reduced pressure to afford a dark green oil. A pure dark green liquid compound was obtained by distillation at 90° C. (30 mTorr). Yield, 34 g, 71%. mp: –17° C. $^1$H NMR(C$_6$D$_6$, 25° C., ppm): –100.7 (br, 3H), –30.6 (br, 9H), 86.7 (br, 3H), 248.5 (br, 2H), 268.8 (br, 2H). Anal. Calcd for CoC$_{18}$H$_{38}$N$_4$: C, 58.52; H, 10.37; N, 15.16. Found: C, 58.36; H, 10.66; N, 14.87.

Example 6

CVD of Cobalt Oxide

CVD from a vapor mixture of bis(N-tert-butyl-N'-ethyl-propionamidinato)cobalt(II), water vapor and nitrogen gas at a substrate temperature of 200° C. produced a film of cobalt (II) oxide, CoO.

Example 7

CVD of Copper Oxide and Formation of Cu Seed Layer

CVD from a vapor mixture of 0.4 Torr (N,N'-di-sec-butyl-acetamidinato)copper(I) dimer, 4 Torr water vapor and 4 Torr nitrogen gas at a substrate temperature of 140° C. produced a film of copper(I) oxide, Cu$_2$O. The Cu$_2$O could be converted to copper metal by reduction for one minute with a hydrogen plasma strong enough to raise the temperature of the film and substrate to about 50° C. during the reduction process.

Example 8

CVD of Copper Oxynitride and Formation of Cu Seed Layer

CVD from a vapor mixture of 0.4 Torr (N,N'-di-sec-butyl-acetamidinato)copper(I) dimer vapor, 3 Torr water vapor, 1

Torr ammonia gas and 4 Torr nitrogen gas at a substrate temperature of 160° C. produced a film of copper(I) oxynitride. RBS analysis gave a composition about $Cu_{0.7}O_{0.2}N_{0.1}$. The copper oxynitride film could be converted to a copper metal film by reduction for one minute with a hydrogen plasma strong enough to raise the temperature of the film and substrate to about 50° C. during the reduction process. The copper metal film was exceptionally smooth, with an RMS roughness about 0.5 nm.

Example 9

CVD of Iron

CVD from a vapor mixture of bis(N-tert-butyl-N'-ethyl-propionamidinato)iron(II), hydrogen and nitrogen gas at a substrate temperature of 230° C. produced a film of metallic iron.

Example 10

CVD of Iron Nitride

CVD from a vapor mixture of bis(N-tert-butyl-N'-ethyl-propionamidinato)iron(II), ammonia and nitrogen gas at a substrate temperature of 180° C. produced a film of electrically conductive iron nitride, $Fe_3N$.

Example 11

CVD of Iron Oxide

CVD from a vapor mixture of about 0.03 Torr bis(N-tert-butyl-N'-ethyl-propionamidinato)iron(II), 0.5 Torr water vapor and 1.5 torr nitrogen gas at a substrate temperature of 150° C. produced a film of iron(II) oxide, FeO.

Example 12

CVD of Manganese

CVD from a vapor mixture of about 0.03 Torr bis(N,N'-diisopropylacetamidinato)manganese(II), 1 Torr hydrogen gas and 1 torr nitrogen gas at a substrate temperature of 400° C. produced a film of electrically conductive manganese metal. Its resistivity is 390 µΩ-cm.

Example 13

CVD of Manganese Oxide

CVD from a vapor mixture of about 0.03 Torr bis(N,N'-diisopropylacetamidinato)manganese(II), 0.5 Torr water vapor and 1.5 torr nitrogen gas at a substrate temperature of 160° C. produced a film of manganese(II) oxide, MnO.

Example 14

CVD of Manganese Nitride

CVD from a vapor mixture of about 0.03 Torr bis(N,N'-diisopropylacetamidinato)manganese(II), 0.5 Torr ammonia and 1.5 torr nitrogen gas at a substrate temperature of 200° C. produced a film of electrically conductive manganese nitride (II), $Mn_3N_2$.

Example 15

CVD of Vanadium Oxide

CVD from a vapor mixture of tris(N,N'-diisopropylacetamidinato)vanadium(III), water vapor and nitrogen gas at a substrate temperature of 250° C. produced a film of electrically conductive vanadium(III) oxide, $V_2O_3$.

Example 16

CVD of Yttrium Oxide

CVD from a vapor mixture of tris(N,N'-diisopropylacetamidinato)yttrium(III), water vapor and nitrogen gas at a substrate temperature of 280° C. produced a film of electrically insulating yttrium(III) oxide, $Y_2O_3$.

Example 17

Deposition of Copper Oxynitride

The deposition of CuON was done in a tube-furnace type reactor which has 36 mm inner diameter (ID). Copper (I) N,N'-di-sec-butylacetamidinate ($[Cu(^sBu\text{-}Me\text{-}amd)]_2$) is used as a Cu precursor, which was delivered by bubbling with 40 sccm of $N_2$ carrier gas. The bubbler temperature was 130° C. which maintained the Cu precursor as a liquid phase because its melting point is 77° C. All the gas lines, bubbler and valves were located in an oven which maintained good temperature uniformity. $H_2O$ was used as an oxygen source, which was evaporated from a reservoir at room temperature without any carrier gas. The flow rate of water vapor was controlled by a needle valve that was calibrated by comparing with the pressure increase of the chamber by a measured $N_2$ flow rate. $NH_3$ was supplied as a nitrogen source, whose flow rate was controlled by a mass flow controller. The total flow rate of reactant gases ($H_2O$ and $NH_3$) was maintained at 40 sccm, and the ratio of $H_2O$ to $NH_3$ was set to the values 40:0, 30:10, 20:20, 10:30 or 0:40. The reaction gases were mixed with Cu precursor vapor in a small (5 mm ID) tube just prior to entering the reactor tube (36 mm ID) to ensure thorough mixing. The films were deposited at substrate temperatures from 140 to 220° C. under a total chamber pressure of 8 Torr. The films were reduced with $H_2$ remote plasma, which heated the substrates from room temperature to temperatures as high as 50° C. A toroidal plasma generator (ASTRON®i type AX7670, MKS) was supplied with 180 sccm of Ar for plasma ignition and 200 sccm of $H_2$ which upon dissociative excitation acted as a reducing agent. The reduction time was varied from 30 to 180 sec. A Si wafer with a 100 nm thermal oxide was used as substrate. Ru was deposited by sputtering to a 20 nm thickness and exposed to the atmosphere prior to CVD.

The surface morphologies of the as-deposited CuON and reduced films were evaluated by an atomic force microscope (Asylum MFP-3D AFM). The thickness and composition of the deposited films were measured using 2 MeV $He^+$ Rutherford backscattering spectroscopy (RBS). The physical thicknesses of CuON and reduced Cu films were measured by AFM after making stripe patterns by photo-lithography and etching in dilute nitric acid. CuON and Cu films were etched with nitric acid diluted by de-ionized water in a volume ratio 1 (acid):40 (water) or 1:10, respectively. The resistivities of reduced Cu films were evaluated by a four-point probe (Miller Design & Equipment FPP-5000). The phases of as-deposited Cu oxynitride and reduced films were evaluated by TEM diffraction (JEOL JEL2010 TEM) using as a substrate a 50 nm thick $Si_3N_4$ membrane TEM grid (TED PELLA, INC, Prod No. 21500-10).

The morphology of the CuON depended on deposition temperature. The films were smooth with RMS roughness of <1 nm. The smoothest film was deposited at 160° C., with surface roughness just slightly larger than the roughness of the Si substrate. The surface grain size of CuON was constant at about 20 nm up to a deposition temperature of 180° C. At 220° C., the film still had a smooth surface morphology (RMS roughness 1.04 nm) and fairly small grain size (ca. 40 nm), although some larger particles were observed. Thus, CuON seed layer can be deposited over the temperature range from about 140° to about 180° C., and even higher, with good surface morphology. The atomic percentages of Cu, O and N were compared at 140, 180 and 200° C. as measured by RBS for films deposited on amorphous carbon substrates. The composition did not change much over that temperature range, indicating that $CuON_x$ is a stable phase under these deposition conditions. In contrast, the morphology of copper compounds such as $Cu_2O$ and $Cu_3N$ were more sensitive to deposition temperature. CuON appeared less affected by deposition temperature, so smooth CuON films were obtained over a wide process window to get uniform composition and morphology.

It is recognized, of course, that those skilled in the art may make various modifications and additions to the processes of the invention without departing from the spirit and scope of the present contribution to the art. Accordingly, it is to be understood that the protection sought to be afforded hereby should be deemed to extend to the subject matter of the claims and all equivalents thereof fairly within the scope of the invention.

We claim:

1. A method of making an integrated circuit interconnect structure formed on a substrate, comprising:

depositing a conformal cobalt nitride layer on a substrate defining an interconnect structure of an integrated circuit structure by chemical vapor deposition from a composition of matter that comprises bis(N-tert-butyl-N'-ethyl propionamidinato) cobalt(II); and depositing a conductive layer comprising copper over the cobalt nitride layer.

2. The method of claim 1, in which the gaseous mixture further comprises a reducing agent.

3. The method of claim 2, in which the reducing agent is dihydrogen.

4. The method of claim 1, wherein at least part of the copper-comprising conductive layer is a deposited by chemical vapor deposition.

5. The method of claim 4, wherein at least part of the copper-comprising conductive layer is deposited by electrochemical deposition.

6. The method of claim 1, wherein at least part of the copper-comprising conductive layer is deposited from a gaseous mixture comprising a vapor of a copper amidinate.

7. The method of claim 6, wherein the copper amidinate has the formula $[Cu(AMD)]_2$, and the structure

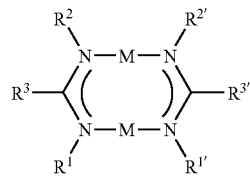

in which M is copper, $R^1$, $R^2$, $R^3$, $R^{1'}$, $R^{2'}$ and $R^{3'}$ may be chosen independently from hydrogen, alkyl, aryl, alkenyl, alkynyl, trialkylsilyl or fluoroalkyl groups or other non-metal atoms or groups.

8. The method of claim 6, wherein the gaseous mixture comprises an oxygen-containing compound and a copper oxide is deposited in a first deposition step.

9. The method of claim 6, wherein the gaseous mixture comprises an oxygen-containing compound and a nitrogen containing compound and a copper oxynitride is formed in a first deposition step.

10. The method of claim 9, further comprising exposing the copper oxynitride to a reducing agent.

11. The method of claim 10, further comprising exposing the copper oxide to a reducing agent.

12. The method of forming a metal-comprising layer by chemical vapor deposition comprising:

exposing a substrate to a gaseous mixture comprising vapors of one or more metal amidinate selected from the metals lithium, sodium, potassium, beryllium, calcium, strontium, barium, scandium, yttrium, lanthanum and the other lanthanide metals, titanium, zirconium, hafnium, vanadium, niobium, tantalum, molybdenum, tungsten, manganese, rhenium, iron, ruthenium, cobalt, rhodium, nickel, palladium, silver, zinc, cadmium, tin, lead, antimony and bismuth.

13. The method of claim 12, in which the gaseous mixture comprises a nitrogen-containing gas.

14. The method of claim 13, in which the nitrogen-containing gas is ammonia or hydrazine.

15. The method of claim 14, in which the gaseous mixture further comprises a reducing agent.

16. The method of claim 15, in which the reducing agent is dihydrogen gas.

17. The method of claim 16, in which the metal amidinate is a cobalt amidinate and the metal-containing layer comprises cobalt nitride.

18. The method of claim 12, in which the gaseous mixture comprises a reducing agent.

19. The method of claim 18, in which the reducing agent is dihydrogen.

20. The method of claim 19, in which the metal amidinate is a cobalt amidinate and the metal-containing layer consists essentially of cobalt metal.

21. The method of claim 12, in which the gaseous mixture comprises an oxygen-containing gas.

22. The method of claim 21, in which the oxygen-containing gas comprises dioxygen, water vapor, ozone, or a per compound.

23. The method of claim 22, in which the metal-comprising layer comprises a metal oxide.

24. The method of claim 23, in which the metal oxide comprises cobalt oxide.

25. A composition of matter for use in a vapor deposition process that comprises bis(N-tert-butyl-N'-ethyl propionamidinato) cobalt(II).

* * * * *